US009681908B2

(12) United States Patent
Garrison

(10) Patent No.: US 9,681,908 B2
(45) Date of Patent: Jun. 20, 2017

(54) JAW ASSEMBLIES FOR ELECTROSURGICAL INSTRUMENTS AND METHODS OF MANUFACTURING JAW ASSEMBLIES

(71) Applicant: COVIDIEN LP, Mansfield, MA (US)

(72) Inventor: David M. Garrison, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 122 days.

(21) Appl. No.: 14/019,031

(22) Filed: Sep. 5, 2013

(65) Prior Publication Data

US 2014/0100568 A1    Apr. 10, 2014

Related U.S. Application Data

(60) Provisional application No. 61/711,075, filed on Oct. 8, 2012.

(51) Int. Cl.
| | | |
|---|---|---|
| *A61B 18/14* | (2006.01) | |
| *A61B 18/08* | (2006.01) | |
| *A61B 18/00* | (2006.01) | |

(52) U.S. Cl.
CPC ........ *A61B 18/085* (2013.01); *A61B 18/1445* (2013.01); *A61B 2018/0063* (2013.01); *A61B 2018/00083* (2013.01); *A61B 2018/00589* (2013.01); *A61B 2018/00595* (2013.01); *A61B 2018/00601* (2013.01); *A61B 2018/1457* (2013.01); *Y10T 29/49826* (2015.01)

(58) Field of Classification Search
CPC .............. A61B 18/085; A61B 18/1445; A61B 2018/1455

USPC .............................................. 606/51, 52, 207
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Thomas Giuliani

(57) ABSTRACT

A jaw assembly includes an electrically-conductive tissue-engaging structure, a jaw member including a support base, and a non-electrically conductive member including a first portion configured to engage the electrically-conductive tissue-engaging structure and a second portion configured to engage the support base of the jaw member. The non-electrically conductive member adapted to electrically isolate the electrically-conductive tissue-engaging structure from the jaw member. The electrically-conductive tissue-engaging structure and the non-electrically conductive member cooperatively define a longitudinally-oriented knife channel therethrough.

15 Claims, 13 Drawing Sheets

(56) References Cited

U.S. PATENT DOCUMENTS

| | | |
|---|---|---|
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| 5,853,412 A * | 12/1998 | Mayenberger ..... A61B 18/1445 606/207 |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,083,618 B2 | 8/2006 | Couture et al. |
| 7,090,673 B2 | 8/2006 | Dycus et al. |
| 7,101,371 B2 | 9/2006 | Dycus et al. |
| 7,101,372 B2 | 9/2006 | Dycus et al. |
| D531,311 S | 10/2006 | Guerra et al. |
| D533,274 S | 12/2006 | Visconti et al. |
| D533,942 S | 12/2006 | Kerr et al. |
| 7,150,097 B2 | 12/2006 | Sremcich et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,255,697 B2 | 8/2007 | Dycus et al. |
| 7,267,677 B2 | 9/2007 | Johnson et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,513,898 B2 | 4/2009 | Johnson et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,282,634 B2 | 10/2012 | Cunningham et al. |
| 8,382,792 B2 | 2/2013 | Chojin |
| 8,439,913 B2 * | 5/2013 | Horner et al. ................. 606/52 |
| 8,939,975 B2 * | 1/2015 | Twomey et al. ............... 606/52 |
| 2002/0188294 A1 | 12/2002 | Couture et al. |
| 2003/0018331 A1 | 1/2003 | Dycus et al. |
| 2004/0082952 A1 | 4/2004 | Dycus et al. |
| 2004/0122423 A1 | 6/2004 | Dycus et al. |
| 2004/0254573 A1 * | 12/2004 | Dycus et al. .................... 606/51 |
| 2007/0173814 A1 | 7/2007 | Hixson et al. |
| 2008/0114356 A1 | 5/2008 | Johnson et al. |
| 2009/0138003 A1 * | 5/2009 | Deville et al. .................. 606/33 |
| 2009/0182327 A1 * | 7/2009 | Unger ............................ 606/46 |
| 2010/0179545 A1 | 7/2010 | Twomey et al. |
| 2010/0204697 A1 | 8/2010 | Dumbauld et al. |
| 2012/0271346 A1 | 10/2012 | Townsend et al. |
| 2013/0046295 A1 | 2/2013 | Kerr et al. |
| 2013/0046303 A1 | 2/2013 | Evans et al. |
| 2013/0046306 A1 | 2/2013 | Evans et al. |
| 2013/0046337 A1 | 2/2013 | Evans et al. |
| 2013/0079774 A1 * | 3/2013 | Whitney et al. ................. 606/52 |
| 2013/0085496 A1 | 4/2013 | Unger et al. |
| 2013/0103035 A1 | 4/2013 | Horner et al. |
| 2013/0116690 A1 | 5/2013 | Unger |
| 2013/0219691 A1 | 8/2013 | Reschke |
| 2014/0100564 A1 * | 4/2014 | Garrison ......................... 606/41 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 3627221 | 2/1988 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1486177 | 12/2004 |
| EP | 1281878 | 10/2005 |
| EP | 1946715 A1 | 7/2008 |
| EP | 1810625 | 8/2009 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 11-47149 | 2/1999 |
| JP | 11-47150 | 2/1999 |
| JP | 11-169381 | 6/1999 |
| JP | 11-192238 | 7/1999 |
| JP | 11-244298 | 9/1999 |

(56) References Cited

FOREIGN PATENT DOCUMENTS

| | | |
|---|---|---|
| JP | 2000-102545 | 4/2000 |
| JP | 2000-135222 | 5/2000 |
| JP | 2000-342599 | 12/2000 |
| JP | 2000-350732 | 12/2000 |
| JP | 2001-8944 | 1/2001 |
| JP | 2001-29355 | 2/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2004-532676 A | 10/2004 |
| JP | 2005-152663 | 6/2005 |
| JP | 2005-523380 A | 8/2005 |
| JP | 2005-253789 | 9/2005 |
| JP | 2005-312807 | 10/2005 |
| JP | 2006-015078 | 1/2006 |
| JP | 2006-501939 | 1/2006 |
| JP | 2006-095316 | 4/2006 |
| JP | 2007-098139 A | 4/2007 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | 03/055449 A1 | 7/2003 |
| WO | WO 2005/110264 | 11/2005 |
| WO | WO 2006/021269 | 3/2006 |
| WO | WO 2008/040483 | 4/2008 |
| WO | WO 2011/018154 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed 6/920/00, Thomas P. Ryan.
U.S. Appl. No. 12/336,970, filed Dec. 17, 2008, Paul R. Sremcich.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012 James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/868,732, filed Apr. 23, 2013, Mueller.
U.S. Appl. No. 13/893,527, filed May 14, 2013, Horner.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 4, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.
U.S. Appl. No. 13/969,278, filed Aug. 16, 2013, Kerr.
U.S. Appl. No. 14/017,572, filed Sep. 4, 2013, Arya.
U.S. Appl. No. 14/019,031, filed Sep. 5, 2013, Garrison.
U.S. Appl. No. 14/019,094, filed Sep. 5, 2013, Garrison.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.

(56) References Cited

OTHER PUBLICATIONS

LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

\* cited by examiner

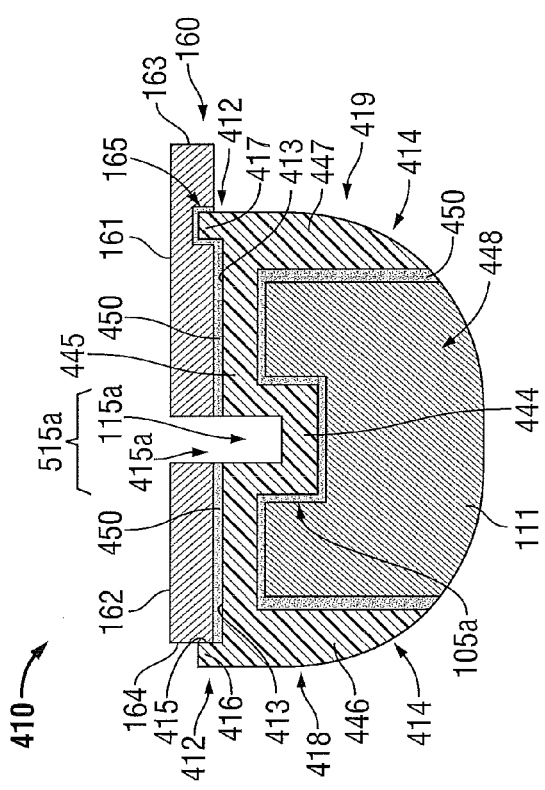
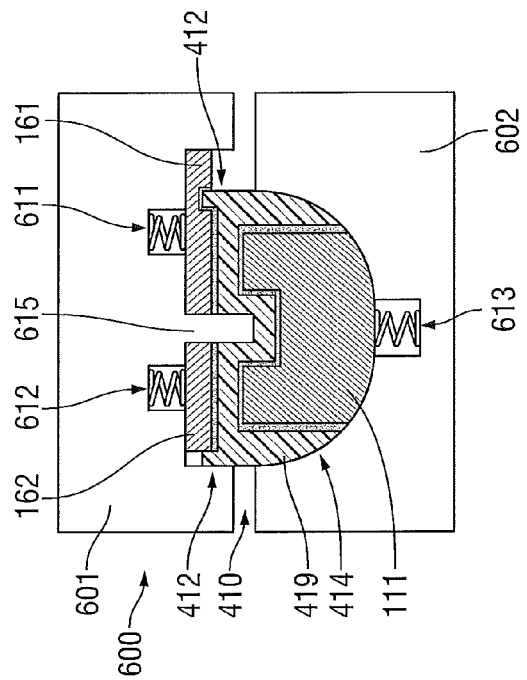

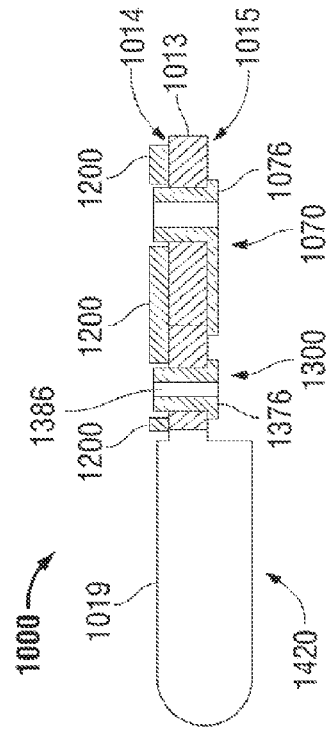
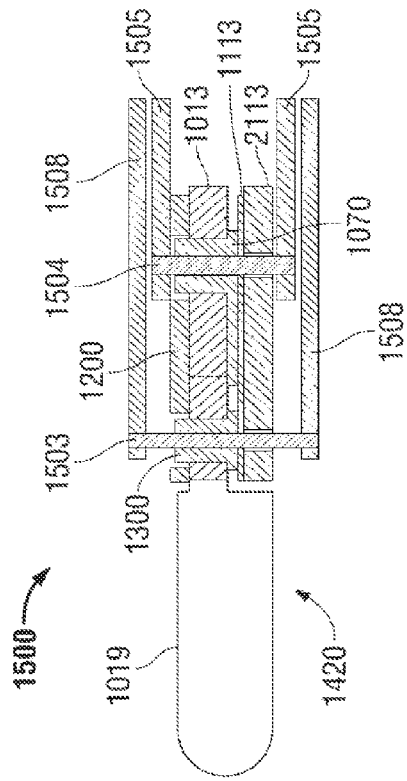
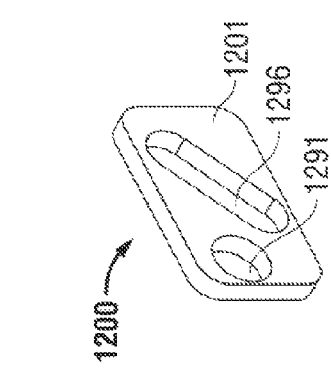
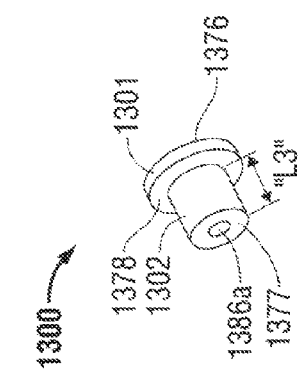

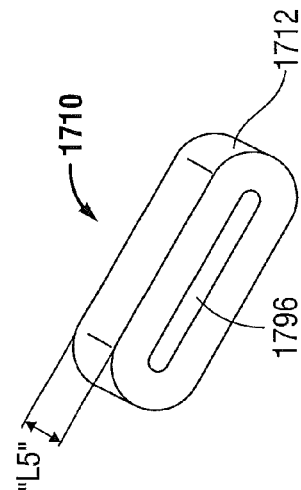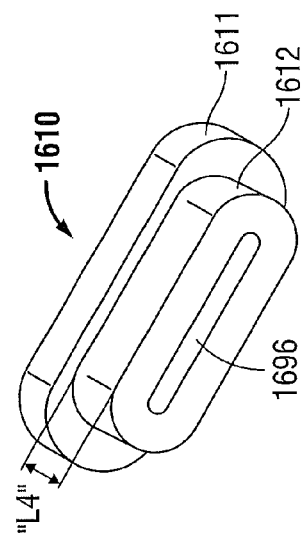

JAW ASSEMBLIES FOR ELECTROSURGICAL INSTRUMENTS AND METHODS OF MANUFACTURING JAW ASSEMBLIES

CROSS REFERENCE TO RELATED APPLICATION

The present application claims the benefit of and priority to U.S. Provisional Application Ser. No. 61/711,075, filed on Oct. 8, 2012, the entire contents of which are incorporated herein by reference.

BACKGROUND

1. Technical Field

The present disclosure relates to electrosurgical instruments. More particularly, the present disclosure relates to jaw assemblies for use in electrosurgical instruments and methods of manufacturing jaw assemblies.

2. Discussion of Related Art

Electrosurgical instruments have become widely used by surgeons. Electrosurgery involves the application of thermal and/or electrical energy to cut, dissect, ablate, coagulate, cauterize, seal or otherwise treat biological tissue during a surgical procedure. Electrosurgery is typically performed using an electrosurgical generator operable to output energy and a handpiece including a surgical instrument (e.g., end effector) adapted to transmit energy to a tissue site during electrosurgical procedures. Electrosurgery can be performed using either a monopolar or a bipolar instrument.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode or pad that is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode. In bipolar electrosurgery, both the active electrode and return electrode functions are performed at the site of surgery. Bipolar electrosurgical devices include two electrodes that are located in proximity to one another for the application of current between their surfaces. Bipolar electrosurgical current travels from one electrode, through the intervening tissue to the other electrode to complete the electrical circuit. Bipolar instruments generally include end-effectors, such as grippers, cutters, forceps, dissectors and the like.

Forceps utilize mechanical action to constrict, grasp, dissect and/or clamp tissue. By utilizing an electrosurgical forceps, a surgeon can utilize both mechanical clamping action and electrosurgical energy to effect hemostasis by heating the tissue and blood vessels to cauterize, coagulate/desiccate, seal and/or divide tissue. Bipolar electrosurgical forceps utilize two generally opposing electrodes that are operably associated with the inner opposing surfaces of end effectors and that are both electrically coupled to an electrosurgical generator. In bipolar forceps, the end-effector assembly generally includes opposing jaw assemblies pivotably mounted with respect to one another. In bipolar configuration, only the tissue grasped between the jaw assemblies is included in the electrical circuit. Because the return function is performed by one jaw assembly of the forceps, no patient return electrode is needed.

By utilizing an electrosurgical forceps, a surgeon can cauterize, coagulate/desiccate and/or seal tissue and/or simply reduce or slow bleeding by controlling the intensity, frequency and duration of the electrosurgical energy applied through the jaw assemblies to the tissue. During the sealing process, mechanical factors such as the pressure applied between opposing jaw assemblies and the gap distance between the electrically-conductive tissue-contacting surfaces (electrodes) of the jaw assemblies play a role in determining the resulting thickness of the sealed tissue and effectiveness of the seal.

A variety of types of end-effector assemblies have been employed for various types of electrosurgery using a variety of types of monopolar and bipolar electrosurgical instruments. Jaw assembly components of end-effector assemblies for use in electrosurgical instruments are required to meet specific tolerance requirements for proper jaw alignment and other closely-toleranced features, and are generally manufactured by expensive and time-consuming processes that typically involve complex machining operations. Gap tolerances and/or surface parallelism and flatness tolerances are parameters that, if properly controlled, can contribute to a consistent and effective tissue seal. Thermal resistance, strength and rigidity of surgical jaw assemblies also play a role in determining the reliability and effectiveness of electrosurgical instruments.

SUMMARY

A continuing need exists for tightly-toleranced jaw assembly components that can be readily integrated into manufacturing assembly processes for the production of end-effector assemblies for use in electrosurgical instruments, such as electrosurgical forceps. Further need exists for the development of a manufacturing process that effectively fabricates jaw assembly components at low cost, and results in the formation of a reliable electrosurgical instrument that meets specific tolerance requirements for proper jaw alignment and other tightly-toleranced jaw assembly features, with reduction or elimination of complex machining operations.

A continuing need exists for a reliable electrosurgical instrument that regulates the gap distance between opposing jaw assemblies, reduces the chances of short circuiting the opposing jaws during activation, and assists in gripping, manipulating and holding tissue prior to and during activation and dividing of the tissue. A continuing need exists for improved thermal resistance, strength and rigidity of jaw assemblies using lower cost technologies.

According to an aspect, a jaw assembly is provided. The jaw assembly includes an electrically-conductive tissue-engaging structure, a jaw member including a support base, and a non-electrically conductive member including a first portion configured to engage the electrically-conductive tissue-engaging structure and a second portion configured to engage the support base of the jaw member. The non-electrically conductive member adapted to electrically isolate the electrically-conductive tissue-engaging structure from the jaw member. The electrically-conductive tissue-engaging structure and the non-electrically conductive member cooperatively define a longitudinally-oriented knife channel therethrough.

According to an aspect, an end-effector assembly is provided. The end-effector assembly includes opposing first and second jaw assemblies pivotably mounted with respect to one another. The first jaw assembly includes a first jaw member including a first arm member defining one or more apertures at least partially therethrough and a first support base extending distally from the first arm member. The second jaw assembly includes a second jaw member including a second arm member defining one or more apertures at least partially therethrough and a second support base extending distally from the second arm member. The first jaw assembly further includes a first electrically-conductive tissue-engaging structure and a first non-electrically conductive member. The first non-electrically conductive member includes a first portion configured to engage the first electrically-conductive tissue-engaging structure and a second portion configured to engage the first support base of the first jaw member. The second jaw assembly further includes a second electrically-conductive tissue-engaging structure and a second non-electrically conductive member. The second non-electrically conductive member includes a first portion configured to engage the second electrically-conductive tissue-engaging structure and a second portion configured to engage the second support base of the second jaw member. One or more pivot pins are engaged with the one or more apertures of the first and second jaw members such that the first and second jaw assemblies are pivotably mounted with respect to one another.

The first jaw assembly and/or the second jaw assembly may be adapted to connect the electrically-conductive tissue-engaging structure associated therewith to an electrosurgical generator According to another aspect, a method of manufacturing a jaw assembly is provided. The method includes the initial steps of providing an electrically-conductive tissue-engaging structure, providing a jaw member including a support base, and providing a non-electrically conductive member including a first portion configured to engage the electrically-conductive tissue-engaging structure and a second portion configured to engage the support base of the jaw member. The non-electrically conductive member is adapted to electrically isolate the electrically-conductive tissue-engaging structure from the jaw member. The method also includes the steps of providing a fixture assembly configured to hold the electrically-conductive tissue-engaging structure in position with respect to the first portion of the non-electrically conductive member and to hold the support base in position with respect to the second portion of the non-electrically conductive member, and performing a brazing process to join the electrically-conductive tissue-engaging structure, non-electrically conductive member and the jaw member using the fixture assembly, thereby forming a jaw assembly.

BRIEF DESCRIPTION OF THE DRAWINGS

Objects and features of the presently-disclosed jaw assemblies for use in electrosurgical instruments and methods of manufacturing jaw assemblies will become apparent to those of ordinary skill in the art when descriptions of various embodiments thereof are read with reference to the accompanying drawings, of which:

FIG. 5 is an enlarged, cross-sectional view taken along the section lines 5-5 of FIG. 4;

FIG. 6 is an enlarged, cross-sectional view of the jaw assembly of FIG. 5 shown disposed within a fixture assembly, such as during an assembly process, in accordance with an embodiment of the present disclosure;

FIG. 12 is an enlarged, perspective view of the electrically-insulative jaw insert shown in FIG. 11A;

FIG. 13 is an enlarged, perspective view of the first electrically-insulative bushing shown in FIG. 10A;

FIG. 14 is an enlarged, cross-sectional view of the jaw assembly of FIGS. 10A and 11A, including the electrically-insulative jaw insert shown in FIG. 12, the first electrically-insulative bushing shown in FIG. 13, and the second electrically-insulative bushing shown in FIG. 10B in accordance with an embodiment of the present disclosure;

FIG. 15 is an enlarged, cross-sectional view of an end-effector assembly including the jaw assembly of FIG. 14 in accordance with an embodiment of the present disclosure;

FIG. 16A is a perspective view of another embodiment of an electrically-insulative bushing in accordance with the present disclosure;

FIG. 16B is a perspective view of yet another embodiment of an electrically-insulative bushing in accordance with the present disclosure;

FIG. 17A is a perspective view of an electrically-insulative tubular bushing in accordance with an embodiment of the present disclosure;

FIG. 17B is a perspective view of an oblong electrically-insulative bushing in accordance with an embodiment of the present disclosure;

DETAILED DESCRIPTION

Figure 1:
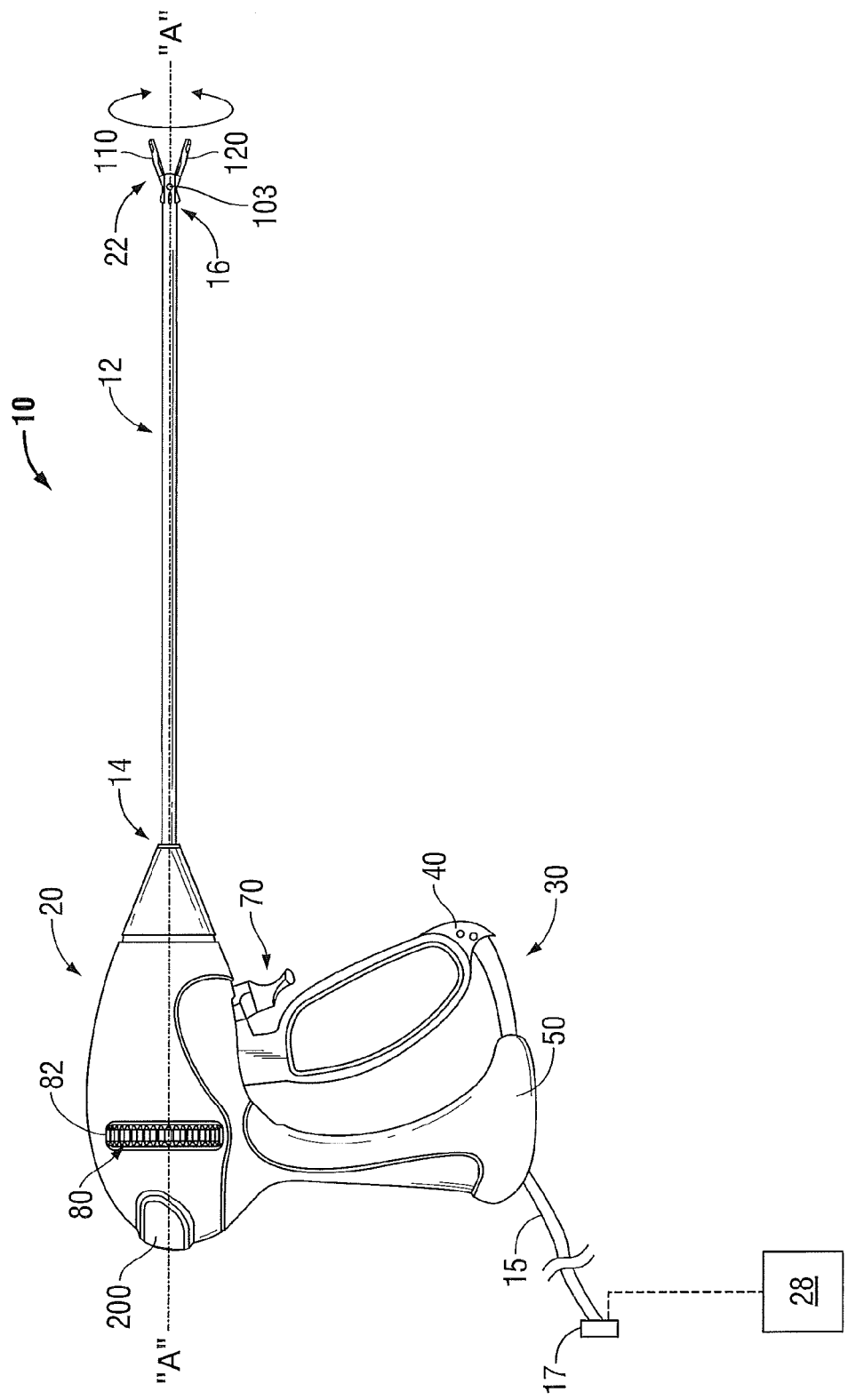
FIG. 1 is a right, side view of an endoscopic bipolar forceps showing a housing, a rotatable member, a shaft and an end-effector assembly in accordance with an embodiment of the present disclosure.

Hereinafter, embodiments of jaw assemblies for use in electrosurgical instruments and methods of manufacturing jaw assemblies of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

Various embodiments of the present disclosure provide electrosurgical instruments suitable for sealing, cauterizing, coagulating/desiccating and/or cutting vessels and vascular tissue. Various embodiments of the present disclosure provide an electrosurgical forceps with an end-effector assembly including opposing jaw assemblies pivotably mounted with respect to one another. Various embodiments of the present disclosure provide jaw assemblies formed to meet specific tolerance requirements for proper jaw alignment, thermal resistance, strength and rigidity. Various embodiments of the present disclosure provide methods of manufacturing jaw assembly components of end-effector assemblies for use in electrosurgical instruments, including without limitation, bipolar forceps.

Embodiments of the presently-disclosed electrosurgical forceps may be suitable for utilization in endoscopic surgical procedures and/or suitable for utilization in open surgical applications. Embodiments of the presently-disclosed bipolar forceps may be implemented using electromagnetic radiation at microwave frequencies, radio frequencies (RF) or at other frequencies.

Although the following description describes the use of an endoscopic bipolar forceps, the teachings of the present disclosure may also apply to a variety of electrosurgical devices that include jaw assemblies.

In FIG. 1, an embodiment of an endoscopic bipolar forceps 10 is shown for use with various surgical procedures and generally includes a housing 20, a handle assembly 30, a rotatable assembly 80, a trigger assembly 70 and an end-effector assembly 22 that mutually cooperate to grasp, seal and/or divide tissue, e.g., tubular vessels and vascular tissue (not shown). Although FIG. 1 depicts a bipolar forceps 10 for use in connection with endoscopic surgical procedures, the teachings of the present disclosure may also apply to more traditional open surgical procedures. For the purposes herein, the forceps 10 is described in terms of an endoscopic instrument; however, an open version of the forceps (e.g., bipolar forceps 200 shown in FIG. 2) may also include the same or similar operating components and features as described below.

Forceps 10 includes a shaft 12 having a distal end 16 configured to mechanically engage the end-effector assembly 22 and a proximal end 14 configured to mechanically engage the housing 20. In some embodiments, the shaft 12 has a length from the proximal side of the handle assembly 30 to the distal side of the forceps 10 in a range of about 7 centimeters to about 44 centimeters. End-effector assembly 22 may be selectively and releaseably engageable with the distal end 16 of the shaft 12, and/or the proximal end 14 of the shaft 12 may be selectively and releaseably engageable with the housing 20 and the handle assembly 30.

The proximal end 14 of the shaft 12 is received within the housing 20, and connections relating thereto are disclosed in commonly assigned U.S. Pat. No. 7,150,097 entitled "METHOD OF MANUFACTURING JAW ASSEMBLY FOR VESSEL SEALER AND DIVIDER", commonly assigned U.S. Pat. No. 7,156,846 entitled "VESSEL SEALER AND DIVIDER FOR USE WITH SMALL TROCARS AND CANNULAS", commonly assigned U.S. Pat. No. 7,597,693 entitled "VESSEL SEALER AND DIVIDER FOR USE WITH SMALL TROCARS AND CANNULAS" and commonly assigned U.S. Pat. No. 7,771,425 entitled "VESSEL SEALER AND DIVIDER HAVING A VARIABLE JAW CLAMPING MECHANISM".

Forceps 10 includes an electrosurgical cable 15. Electrosurgical cable 15 may be formed from a suitable flexible, semi-rigid or rigid cable, and may connect directly to an electrosurgical power generating source 28. In some embodiments, the electrosurgical cable 15 connects the forceps 10 to a connector 17, which further operably connects the instrument 10 to the electrosurgical power generating source 28. Cable 15 may be internally divided into one or more cable leads (e.g., 325a and 325b shown in FIGS. 7 and 8, respectively) each of which transmits electrosurgical energy through their respective feed paths to the end-effector assembly 22.

Electrosurgical power generating source 28 may be any generator suitable for use with electrosurgical devices, and may be configured to provide various frequencies of electromagnetic energy. Examples of electrosurgical generators that may be suitable for use as a source of electrosurgical energy are commercially available under the trademarks FORCE EZ™, FORCE FX™, and FORCE TRIAD™ offered by Covidien Surgical Solutions of Boulder, Colo. Forceps 10 may alternatively be configured as a wireless device or battery-powered.

End-effector assembly 22 generally includes a pair of opposing jaw assemblies 110 and 120 pivotably mounted with respect to one another. End-effector assembly 22 may be configured as a bilateral jaw assembly, i.e., both jaw assemblies 110 and 120 move relative to one another. Alternatively, the forceps 10 may include a unilateral assembly, i.e., the end-effector assembly 22 may include a stationary or fixed jaw assembly, e.g., 120, mounted in fixed relation to the shaft 12 and a pivoting jaw assembly, e.g., 110, mounted about a pivot pin 103 coupled to the stationary jaw assembly. Jaw assemblies 110 and 120 may be curved at various angles to facilitate manipulation of tissue and/or to provide enhanced line-of-sight for accessing targeted tissues.

As shown in FIG. 1, the end-effector assembly 22 is rotatable about a longitudinal axis "A-A" through rotation, either manually or otherwise, of the rotatable assembly 80.

Rotatable assembly 80 generally includes two halves (not shown), which, when assembled about a tube of shaft 12, form a generally circular rotatable member 82. Rotatable assembly 80, or portions thereof, may be configured to house a drive assembly (not shown) and/or a knife assembly (not shown), or components thereof. A reciprocating sleeve (not shown) is slidingly disposed within the shaft 12 and remotely operable by the drive assembly (not shown). Examples of rotatable assembly embodiments, drive assembly embodiments, and knife assembly embodiments of the forceps 10 are described in the above-mentioned, commonly-assigned U.S. Pat. Nos. 7,150,097, 7,156,846, 7,597,693 and 7,771,425.

Handle assembly 30 includes a fixed handle 50 and a movable handle 40. In some embodiments, the fixed handle 50 is integrally associated with the housing 20, and the movable handle 40 is selectively movable relative to the fixed handle 50. Movable handle 40 of the handle assembly 30 is ultimately connected to the drive assembly (not shown). As can be appreciated, applying force to move the movable handle 40 toward the fixed handle 50 pulls the drive sleeve (not shown) proximally to impart movement to the jaw assemblies 110 and 120 from an open position, wherein the jaw assemblies 110 and 120 are disposed in spaced relation relative to one another, to a clamping or closed position, wherein the jaw assemblies 110 and 120 cooperate to grasp tissue therebetween. Examples of handle assembly embodiments of the forceps 10 are described in the above-mentioned, commonly-assigned U.S. Pat. Nos. 7,150,097, 7,156,846, 7,597,693 and 7,771,425.

Forceps 10 includes a switch 200 configured to permit the user to selectively activate the forceps 10 in a variety of different orientations, i.e., multi-oriented activation. As can be appreciated, this simplifies activation. When the switch 200 is depressed, electrosurgical energy is transferred through one or more electrical leads (e.g., leads 325a and 325b shown in FIGS. 7 and 8, respectively) to the jaw assemblies 110 and 120. Although FIG. 1 depicts the switch 200 disposed at the proximal end of the housing assembly 20, switch 200 may be disposed on another part of the forceps 10 (e.g., the fixed handle 50, rotatable member 82, etc.) or another location on the housing assembly 20.

Figure 2:
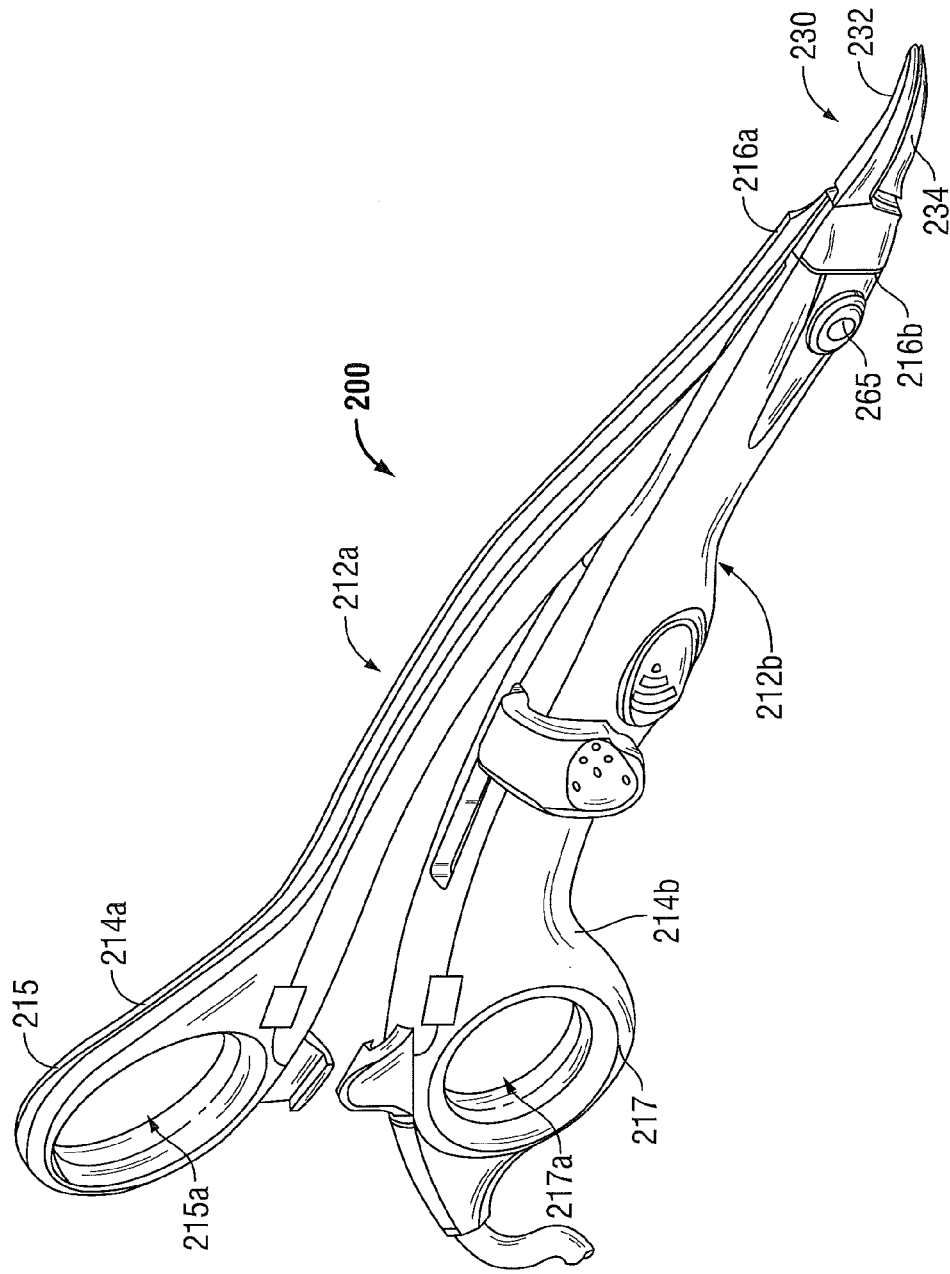
FIG. 2 is a perspective view of an open bipolar forceps according to an embodiment of the present disclosure.

In FIG. 2, an embodiment of an open forceps 200 is shown for use with various surgical procedures and generally includes a pair of opposing shafts 212a and 212b having an end effector assembly 230 attached to the distal ends 216a and 216b thereof, respectively. End effector assembly 230 includes a pair of opposing jaw members 232 and 234 that are pivotably connected about a pivot pin 265 and movable relative to one another to grasp tissue. Each shaft 212a and 212b includes a handle 215 and 217, respectively, disposed at the proximal end 214a and 214b thereof, respectively. Each handle 215 and 217 defines a finger and/or thumb hole 215a and 217a, respectively, therethrough for receiving the user's finger or thumb. Finger and/or thumb holes 215a and 217a facilitate movement of the shafts 212a and 212b relative to one another to pivot the jaw members 232 and 234 from an open position, wherein the jaw members 232 and 234 are disposed in spaced relation relative to one another, to a clamping or closed position, wherein the jaw members 232 and 234 cooperate to grasp tissue therebetween.

Figure 3B:
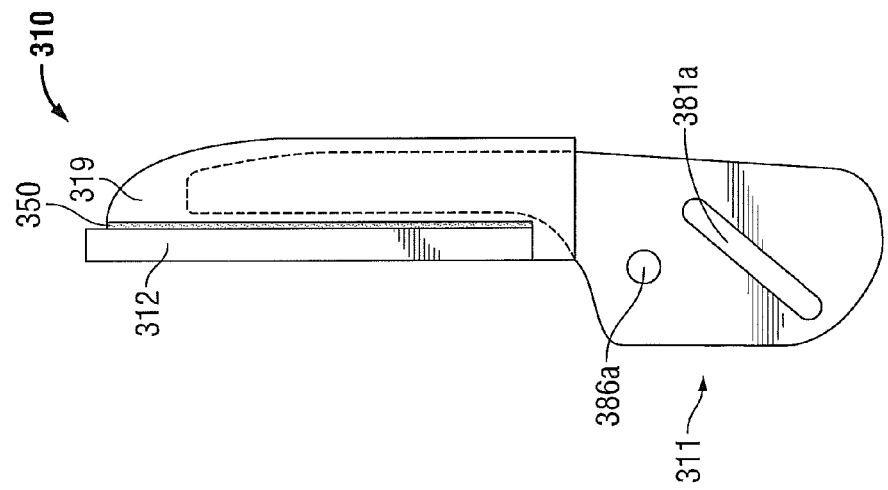
FIG. 3B is a side view of the jaw assembly shown in FIG. 3A.
Figure 3A:
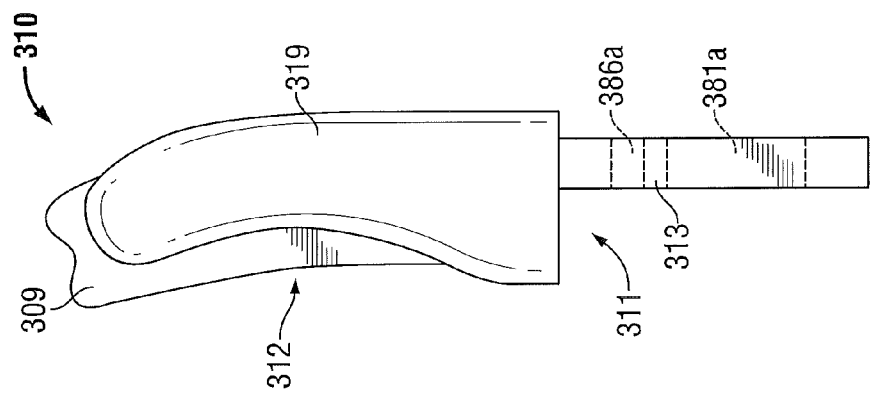
FIG. 3A is a schematic diagram of a jaw assembly including an electrode tip portion in accordance with an embodiment of the present disclosure.

FIGS. 3A and 3B show a jaw assembly (shown generally as 310 in FIGS. 3A and 3B) according to an embodiment of the present disclosure that includes a jaw member 311 and an electrically-conductive tissue-engaging surface or sealing plate 312. Jaw member 311 includes a support base 319 that extends distally from an arm member 313. Jaw member 311 may define one or more apertures at least partially therethrough, e.g., pivot holes and/or pin slots or openings. In some embodiments, the jaw member 311 includes an elongated angled slot 381a and a pivot hole 386a (shown in phantom lines in FIG. 3A) defined therethrough.

Sealing plate 312 includes an electrode tip portion 309 for contacting tissue. Electrode tip portion 309 may be monopolar or bipolar. Electrode tip portion 309 may be configured to provide a desired function, and may include curves at various angles to facilitate contact with targeted tissue. Electrode tip portion 309 may include a sharp knife edge, a blunt tip, a blunt edge, paddle, hook, a ball-shaped portion, or another shape.

FIGS. 4 through 7 show a jaw assembly 410 according to an embodiment of the present disclosure that includes a jaw member 111, an electrically-conductive tissue-engaging surface or sealing plate 160, and a non-electrically conductive member 419. In some embodiments, the sealing plate 160 may include an electrode tip portion, e.g., similar to the electrode tip portion 309 of the sealing plate 312 shown in FIG. 3. Non-electrically conductive member 419 is generally formed of an electrically insulative material and defines a first portion 412 (FIG. 5) configured to engage the sealing plate 160 and a second portion 414 (FIG. 5) configured to engage the jaw member 111, or component thereof (e.g., support base 119 shown in FIG. 7). In some embodiments, the support base 119 includes an inner-facing surface 118 (FIG. 7) configured to support at least a portion of the non-electrically conductive member 419 thereon.

Figure 7:
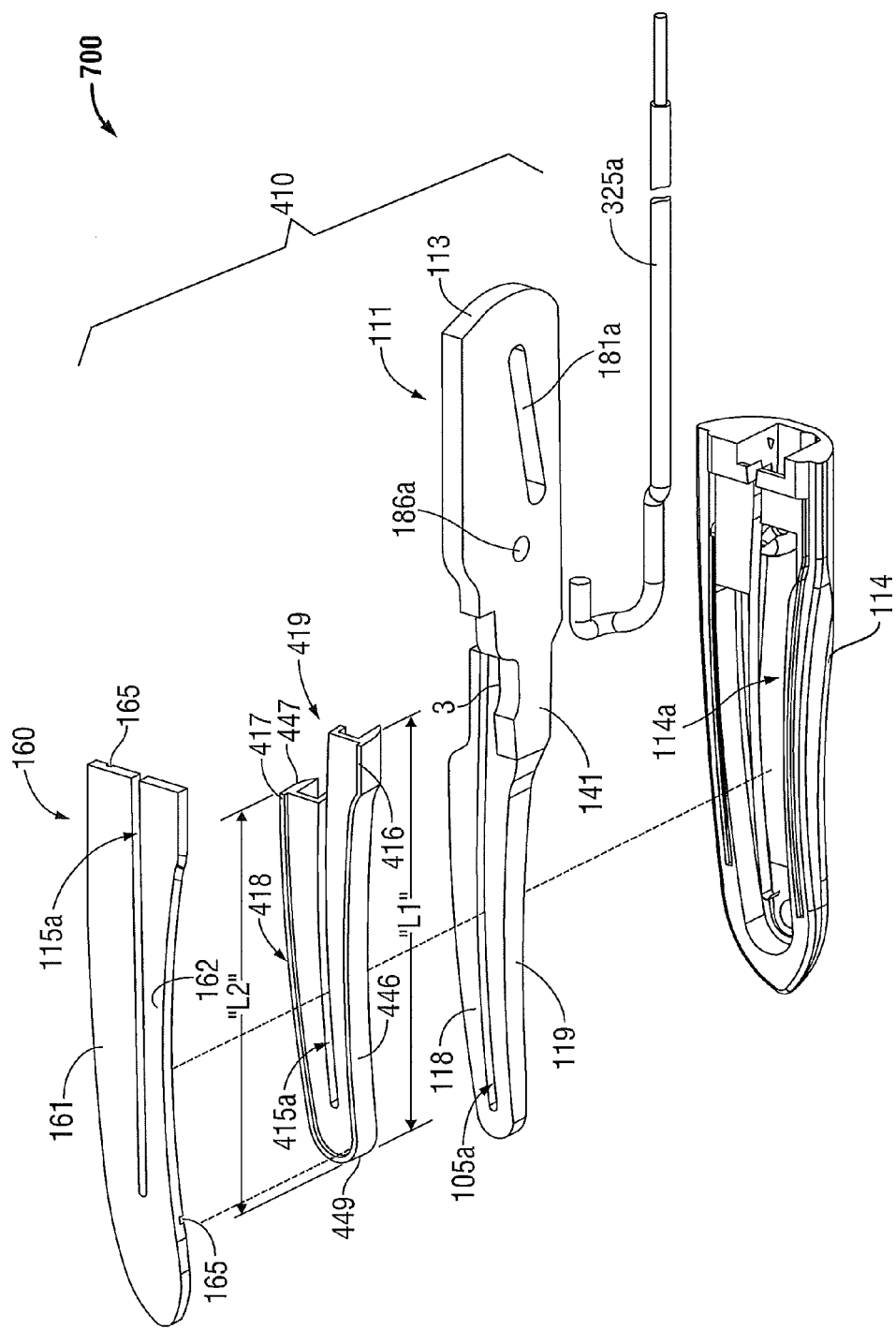
FIG. 7 is an enlarged, perspective view of an embodiment of an upper jaw assembly of an end-effector assembly, such as the end-effector assembly of the forceps shown in FIG. 1, with parts separated in accordance with the present disclosure.

As shown in FIGS. 5 and 7, the sealing plate 160 includes a knife-channel portion 115a, the non-electrically conductive member 419 includes a knife-channel portion 415a, and the jaw member 111 includes a central channel 105a, which when assembled, form a longitudinally-oriented slot or knife channel 515a (FIG. 5) defined therethrough for reciprocation of a knife blade (not shown). In some embodiments, as shown in FIG. 5, the bottom of the knife channel 515a may extend below a plane (not shown) containing the upper surface of the jaw member 111, e.g. to improve strength and/or rigidity of the jaw assembly 410. In alternative embodiments (not necessarily shown), the bottom of the knife channel 515a may be disposed above a plane (not shown) containing the upper surface of the jaw member 111, e.g., depending upon the height of the knife blade (not shown) and/or the material properties of the material(s) used to form the non-electrically conductive member 419.

Jaw member 111, which is described in more detail later in this description, may define one or more apertures at least partially therethrough, e.g., pivot holes and/or pin slots or openings. An embodiment of a jaw member, such as the jaw assembly 111 of FIGS. 4 and 5, in accordance with the present disclosure, is shown in more detail in FIG. 7. It will be understood, however, that other jaw member embodiments may also be used. In some embodiments, as shown in FIGS. 4 and 7, the jaw member 111 includes an elongated angled slot 181a and a pivot hole 186a defined therethrough.

Figure 4:
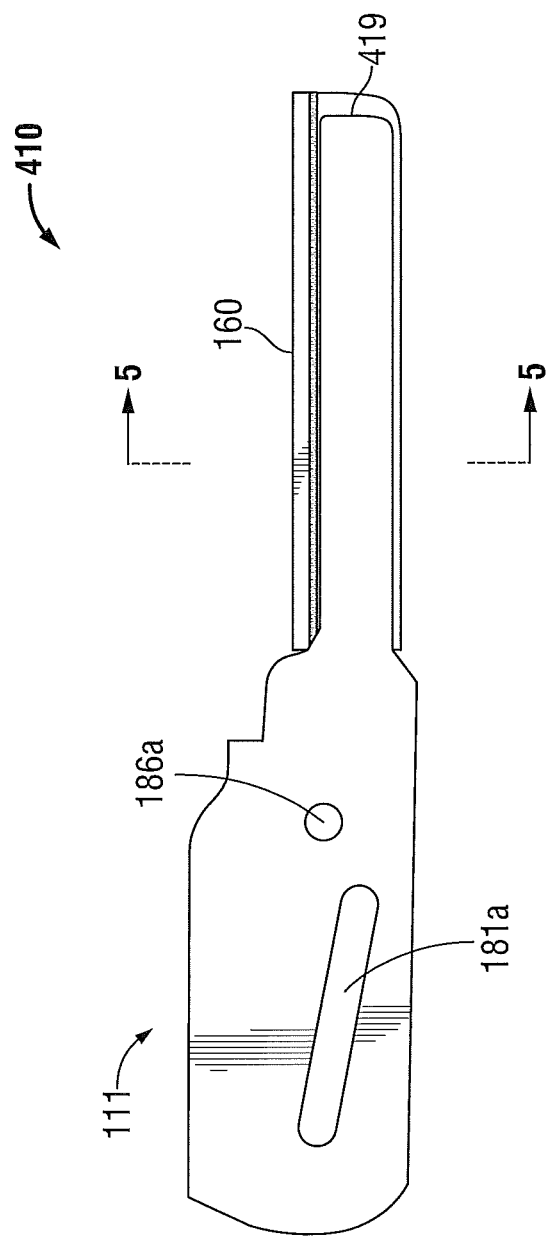
FIG. 4 is a schematic diagram of a jaw assembly in accordance with an embodiment of the present disclosure.

An embodiment of a sealing plate, such as sealing plate 160 of FIGS. 4 and 5, in accordance with the present disclosure, is shown in more detail in FIG. 7. It will be understood, however, that other sealing plate embodiments may also be used. Sealing plate 160 generally includes a first portion 161 and a second portion 162, and may include an electrode tip portion (e.g., electrode tip portion 309 shown in FIG. 3). First portion 161 and the second portion 162 of the sealing plate 160 are at least partially separated by a longitudinally-oriented slot or knife-channel portion 115a defined therebetween.

Non-electrically conductive member 419 is configured to electrically isolate, at least in part, the sealing plate 160 from the jaw member 111. Non-electrically conductive member 419 includes a knife-channel portion 415a defined therein which extends longitudinally along a portion of the non-electrically conductive member 419 and which aligns in vertical registration with the knife-channel portion 115a defined in the sealing plate 160 to facilitate translation of the distal end of the knife (not shown) therethrough.

Non-electrically conductive member 419 may be formed of any suitable electrically insulative material, e.g., non-electrically conductive composite materials, with desired material characteristics. In some embodiments, non-electrically conductive member 419 is formed of non-electrically conductive ceramic, and may provide enhanced thermal resistance, strength, and/or rigidity of the jaw assembly 410. In alternative embodiments not shown, non-electrically conductive member 419 may be formed of a combination of electrically-conductive materials, partially electrically-conductive materials, and/or non-electrically conductive materials. Non-electrically conductive member 419 may be formed as a multi-layer configuration of materials. Non-electrically conductive member 419 may be formed by any suitable process, e.g., injection molding, ceramic injection molding (CIM), or compression molding.

As shown in FIGS. 5 and 7, the non-electrically conductive member 419 includes a body 418 defining a first lateral side portion 446 having a first length "L1", a second lateral side portion 447 having a second length "L2", and an upper portion 445 disposed between the first and second lateral side portions 446 and 447, respectively. First and second lateral side portions 446 and 447, respectively, are joined at one end by an apex 449 (FIG. 7) disposed at the distal end of the body 418 and spaced apart at opposing ends to define an opening 448 (FIG. 5) therebetween. Upper portion 445 includes a generally U-shaped wall portion 444 defining the knife-channel portion 415a. As shown in FIG. 5, at least a portion of the wall portion 444 is disposed within the central channel 105a of the jaw member 111.

The first and second lengths "L1" and "L2" of the first and second lateral side portions 446 and 447, respectively, may depend on the configuration of the jaw member 111, or component thereof (e.g., support base 119), and/or the configuration of the sealing plate 160. In some embodiments, as shown in FIG. 7, the first length of the first lateral side portion 446 is different than the second length of the second lateral side portion 447. In alternative embodiments not shown, the first and second lengths "L1" and "L2" of the first and second lateral side portions 446 and 447, respectively, may be substantially the same, e.g., depending on the configuration of the jaw member and/or the configuration of the sealing plate.

As shown in FIG. 5, the first portion 412 of the non-electrically conductive member 419 includes a first surface 413 and a shoulder region 416 extending outwardly beyond the first surface 413 along at least a portion of the first lateral side portion 446. In some embodiments, as shown in FIG. 5, the first surface 413 is configured to support the first portion 161 of the sealing plate 160 and to support at least a portion of the second portion 162 of the sealing plate 160.

First surface 413 is configured to support at least a portion of the sealing plate 160, and may be a substantially flat surface. In alternative embodiments not shown, the non-electrically conductive member 419 may include texturized surface areas disposed on, or otherwise associated with, the first surface 413 on either one or both sides of the longitudinally-oriented knife-channel portion 415a. The texturized surface areas may include any suitable type of texturized surface or pattern formed by any suitable process.

Sealing plate 160 may be affixed atop the first surface 413 of the first portion 412 of the non-electrically conductive member 419 in any suitable manner, e.g., joined by brazing and/or adhesive bonding. As shown in FIG. 5, material 450, e.g., brazing material or adhesive material, may be disposed between the sealing plate 160 and the non-electrically conductive member 419, e.g., to facilitate assembly and/or provide strength and rigidity.

Shoulder region 416 may be configured to provide strength and/or rigidity. Shoulder region 416 generally includes an inner wall 415 located to facilitate the proper alignment of the sealing plate 160, e.g., to vertically align the knife-channel portion 115a of the sealing plate 160 in relation to the knife-channel portion 415a of the non-electrically conductive member 419, such as during assembly of the jaw member 410. In some embodiments, as shown in FIG. 5, the inner wall 415 is configured to engage a side portion of the second portion 162 of the sealing plate 160. The shape and size of the shoulder region 416 may be varied from the configuration depicted in FIG. 5.

In some embodiments, as shown in FIG. 5, the first portion 412 of the non-electrically conductive member 419 includes a flange 417 extending outwardly beyond the first surface 413 along at least a portion of the second lateral side portion 447, e.g., to facilitate the positioning and/or secure attachment of the sealing plate 160 to the non-electrically conductive member 419. Flange 417 is configured to engage a recess or channel 165 defined in the second portion 162 of the sealing plate 160. The shape, size and location of the flange 417 may be varied from the configuration depicted in FIG. 5.

Second portion 414 of the non-electrically conductive member 419 includes the inner surface of the first lateral side portion 446, inner surface of the second lateral side portion 447, and the inner surface of the upper portion 445 disposed between the first and second lateral side portions 446 and 447, respectively. The opening 448 defined by the inner surfaces of the first and second lateral side portions 446, 447 and the upper portion 445 is configured to receive the jaw member 111 therein. As shown in FIG. 5, material 450, e.g., brazing material or adhesive material, may be disposed between the jaw member 111 and the inner surfaces of the first and second lateral side portions 446, 447 and the upper portion 445, e.g., to facilitate assembly and/or provide strength and rigidity. In alternative embodiments not shown, the inner surface of the first lateral side portion 446, inner surface of the second lateral side portion 447, and/or the inner surface of the upper portion 445 may include detents, tongue and groove interfaces, locking tabs, adhesive ports, etc., utilized either alone or in combination for assembly purposes.

Sealing plate 160 and the non-electrically conductive member 419, when assembled, including the second portion 162 of the sealing plate 160 disposed adjacent to the shoulder region 416 of the non-electrically conductive member 419, and/or the flange 417 of the non-electrically conductive member 419 received in the channel 165 of the first portion 161 of the sealing plate 160, may increase stability of the knife channel and/or provide increased jaw assembly integrity, and/or may facilitate and/or improve knife-blade reciprocation, and/or may result in improved tissue-cutting capabilities.

Non-electrically conductive member 419 may be used for joining together sealing plates and support bases of jaw members of varied geometries, e.g., lengths and curvatures, or having additional, fewer, or different features than the first and second support bases 119, 129, such that variously-configured jaw assemblies may be fabricated and assembled into various end-effector configurations, e.g., depending upon design of specialized electrosurgical instruments.

FIG. 6 shows a fixture assembly (shown generally as 600 in FIG. 6) according to an embodiment of the present disclosure that includes a first fixture member 601 and a second fixture member 602. Fixture assembly 600 is adapted to releaseably, securely hold the jaw member 111, the sealing plate 160, and the non-electrically conductive member 419 in position relative to one another to facilitate brazing, bonding, or otherwise joining, the jaw member 111, the sealing plate 160, and the non-electrically conductive member 419.

First fixture member 601 is configured to releaseably engage an upper portion of the sealing plate 160 and at least a portion of the first portion 412 of the non-electrically conductive member 419. First fixture member 601 may include one or more securing mechanisms (e.g., two securing mechanisms 611 and 612 shown in FIG. 6) adapted to securely hold the sealing plate 160 in engagement with the first portion 412 of the non-electrically conductive member 419, e.g., to achieve desired alignment conditions. In some embodiments, as shown in FIG. 6, the first fixture member 601 includes a first securing mechanism 611, e.g., adapted to securely hold the first portion 161 of the sealing plate 160 in engagement with the non-electrically conductive member 419, and a second securing mechanism 612, e.g., adapted to securely hold the second portion 162 of the sealing plate 160 in engagement with the non-electrically conductive member 419.

Second fixture member 602 is configured to releaseably engage a bottom portion of the jaw member 111, and may be configured to releaseably engage at least a portion of the second portion 414 of the non-electrically conductive member 419. In some embodiments, as shown in FIG. 6, the second fixture member 602 includes a third securing mechanism 613, e.g., adapted to securely hold the jaw member 111 in engagement with the non-electrically conductive member 419. First, second, and third securing mechanisms 611, 612 and 613, respectively, may be springs, clips or other releasable fasteners. In some embodiments, the first, second, and third securing mechanisms 611, 612 and 613, respectively, may include magnets, vacuum and/or compressed air, and/or adhesive.

Figure 8:
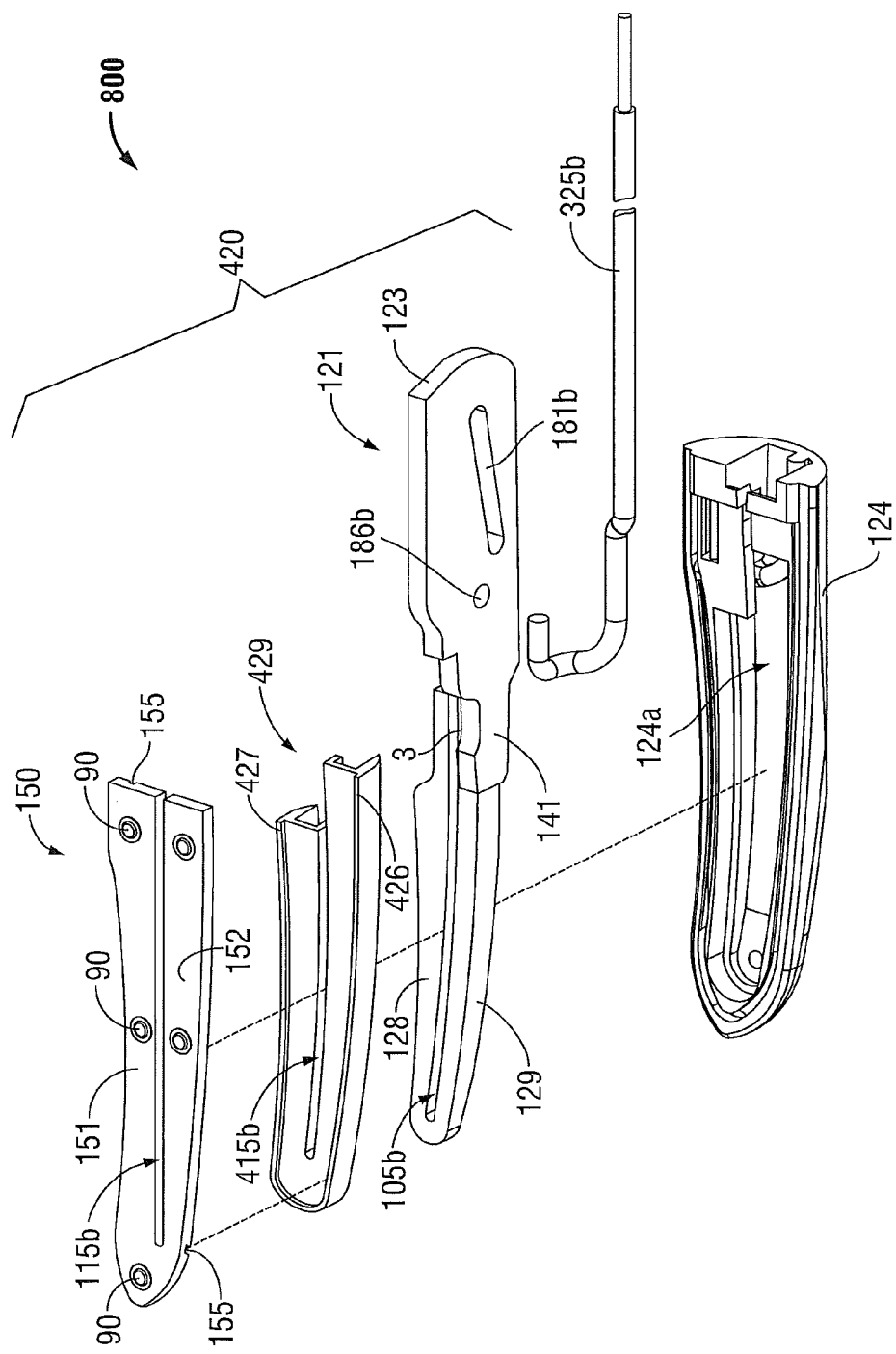
FIG. 8 is an enlarged, perspective view of an embodiment of a lower jaw assembly of an end-effector assembly, such as the end-effector assembly of the forceps shown in FIG. 1, with parts separated in accordance with the present disclosure.

FIG. 7 shows components of a jaw assembly (shown generally as 700 in FIG. 7) according to an embodiment of the present disclosure that includes the jaw assembly 410 shown in FIG. 5. FIG. 8 shows components of a jaw assembly (shown generally as 800 in FIG. 8) according to an embodiment of the present disclosure. Jaw assemblies 700 and 800 may include additional, fewer, or different components than shown in FIGS. 7 and 8, respectively, depending upon a particular purpose or to achieve a desired result.

As shown in FIG. 7, jaw member 111 includes the support base 119 (hereinafter referred to as the "first support base") that extends distally from the arm member 113 (hereinafter referred to as the "first arm member"). First arm member 113 and the first support base 119 are generally formed from metal, e.g., steel, and may include non-metal elements. First arm member 113 and the first support base 119 may be formed from any suitable material or combination of materials. Jaw member 111 may be formed by any suitable process, e.g., machining, stamping, electrical discharge machining (EDM), forging, casting, injection molding, metal injection molding (MIM), and/or fineblanking.

In some embodiments, the first arm member 113 and the first support base 119 are separately fabricated and each includes an engagement structure (not shown) configured for attachment to one another. During a manufacturing process, the engagement structure of the first arm member 113 is welded, joined or otherwise attached to the engagement structure of the first support base 119 along an interface 3 formed therebetween when the respective engagement structures (not shown) are placed in contact with one another, thereby forming the jaw member 111 (hereinafter referred to as the "first jaw member"). Examples of engagement structure embodiments are described in commonly-assigned U.S. patent application Ser. No. 13/243,628 filed on Sep. 23, 2011, entitled "END-EFFECTOR ASSEMBLIES FOR ELECTROSURGICAL INSTRUMENTS AND METHODS OF MANUFACTURING JAW ASSEMBLY COMPONENTS OF END-EFFECTOR ASSEMBLIES".

First arm member 113 may define one or more apertures at least partially therethrough, e.g., pivot holes and/or pin slots or openings. In some embodiments, as shown in FIG. 7, the first arm member 113 includes an elongated angled slot 181a and a pivot hole 186a defined therethrough. The shape, size and spacing of the slot 181a and the pivot hole 186a may be varied from the configuration depicted in FIG. 7. First arm member 113 may include additional, fewer, or different apertures than shown in FIG. 7.

First support base 119 together with the non-electrically conductive member 419 may be encapsulated by the sealing plate 160 and an outer housing 114 having a cavity 114a defined therein. In some embodiments, the outer housing 114 is formed, at least in part, of an electrically non-conductive or substantially electrically non-conductive material. Cavity 114a may be configured to at least partially encapsulate and/or securely engage the first support base 119, the non-electrically conductive member 419 and/or the sealing plate 160.

Examples of sealing plate 160, outer housing 114, and knife blade embodiments are disclosed in commonly assigned International Application Serial No. PCT/US01/11412 filed on Apr. 6, 2001, entitled "ELECTROSURGICAL INSTRUMENT WHICH REDUCES COLLATERAL DAMAGE TO ADJACENT TISSUE", and commonly assigned International Application Serial No. PCT/US01/11411 filed on Apr. 6, 2001, entitled "ELECTROSURGICAL INSTRUMENT REDUCING FLASHOVER".

In some embodiments, jaw assembly 111 is connected to a first electrical lead 325a. Lead 325a, in turn, is electrically coupled with an electrosurgical energy source (e.g., 28 shown in FIG. 1). In some embodiments, lead 325a terminates within the outer housing 114 and is configured to electro-mechanically couple to the sealing plate 160 by virtue of a crimp-like connection (not shown).

As shown in FIG. 8, jaw assembly 800 includes similar elements to jaw assembly 700 of FIG. 7, such as an outer housing 124 having a cavity 124a defined therein and a jaw assembly 420 including an non-electrically conductive member 429 configured to support an electrically-conductive tissue-engaging surface or sealing plate 150 thereon. Cavity 124a may be configured to at least partially encapsulate and/or securely engage the support base 129, the non-electrically conductive member 429, and/or the sealing plate 150.

Second jaw member 121 includes a second support base 129 extending distally from a second arm member 123.

Second arm member 123 and the second support base 129 may be formed from any suitable materials, e.g., metal, or combination of materials. Second arm member 123 may define one or more apertures at least partially therethrough, e.g., pivot holes and/or pin slots or openings. In some embodiments, as shown in FIG. 8, the second arm member 123 includes an elongated angled slot 181b and a pivot hole 186b defined therethrough. In alternative embodiments not shown, the second arm member 123 may include other apertures defined at least partially therethrough.

Similar to like elements of jaw assembly 410, when assembled, the sealing plate 150 and the non-electrically conductive member 429, when assembled, include respective longitudinally-oriented knife channels 115b and 415b defined therethrough for reciprocation of a knife blade (not shown). Sealing plate 150 and the non-electrically conductive member 429, when assembled, including the second portion 152 of the sealing plate 150 disposed adjacent to the shoulder region 426 of the non-electrically conductive member 429, and/or the flange 427 of the non-electrically conductive member 429 received in the channel 155 of the first portion 151 of the sealing plate 160, may increase stability of the knife channel and/or provide increased jaw assembly integrity, and/or may facilitate and/or improve knife-blade reciprocation, and/or may result in improved tissue-cutting capabilities. Jaw assembly 420 shown in FIG. 8 is similar to the jaw assembly 410 shown in FIG. 7, and further description of the like elements is omitted in the interests of brevity.

When the jaw assemblies 700 and 800 are closed about tissue, knife-channel portions 115a, 415a and 115b, 415b form a complete knife channel (not shown) to allow longitudinal extension of the knife blade (not shown) in a distal fashion to sever tissue along a tissue seal. In alternative embodiments, the knife channel may be completely disposed in one of the two jaw assemblies, e.g., jaw assembly 800, depending upon a particular purpose. Jaw assembly 800 may be assembled in a similar manner as described above with respect to jaw assembly 700.

As shown in FIG. 8, jaw assembly 800 is connected to an electrical lead 325b. Lead 325b, in turn, is electrically coupled to an electrosurgical energy source (e.g., 28 shown in FIG. 1). In some embodiments, lead 325b terminates within the outer housing 124 and is configured to electromechanically couple to the sealing plate 150 by virtue of a crimp-like connection (not shown). Leads 325a (FIG. 7) and 325b may allow a user to selectively supply either bipolar or monopolar electrosurgical energy to the jaw assemblies 700 and 800 as needed during surgery.

In some embodiments, as shown in FIG. 8, jaw assembly 800 includes a series of stop members 90 disposed on the inner-facing surfaces of the first portion 151 and the second portion 152 or the sealing plate 150. Stop members 90 may be configured to facilitate and/or enhance the gripping and manipulation of tissue and to control the gap distance (not shown) between opposing jaw assemblies 700 and 800 during the sealing and cutting of tissue. Stop members 90 of varied configurations may be employed on one or both jaw assemblies 700 and 800 depending upon a particular purpose or to achieve a desired result. Examples of stop member embodiments as well as various manufacturing and assembling processes for attaching and/or affixing the stop members 90 to the sealing plate surfaces are described in commonly-assigned International Application Serial No. PCT/US01/11413 filed on Apr. 6, 2001, entitled "VESSEL SEALER AND DIVIDER WITH NON-CONDUCTIVE STOP MEMBERS". In some variations of stop members, compatible with any of the above embodiments, stop members may be printed, patterned, applied, or otherwise deposited using a direct write process, such as by a micro-capillary system, e.g., MICROPEN® technology, or any other suitable material deposition technology.

In alternative embodiments shown in FIGS. 10A through 20, compatible with any of the above embodiments of arm members and support bases for assembly into jaw assembly configurations, an electrically-insulative bushing may be used to electrically isolate the opposing jaw members from one another, wherein a configuration of one or more electrically-insulative bushings may be associated with either or both jaw members.

Hereinafter, a method of manufacturing a jaw assembly is described with reference to FIG. 9. It is to be understood that the steps of the method provided herein may be performed in combination and in a different order than presented herein without departing from the scope of the disclosure.

Figure 9:
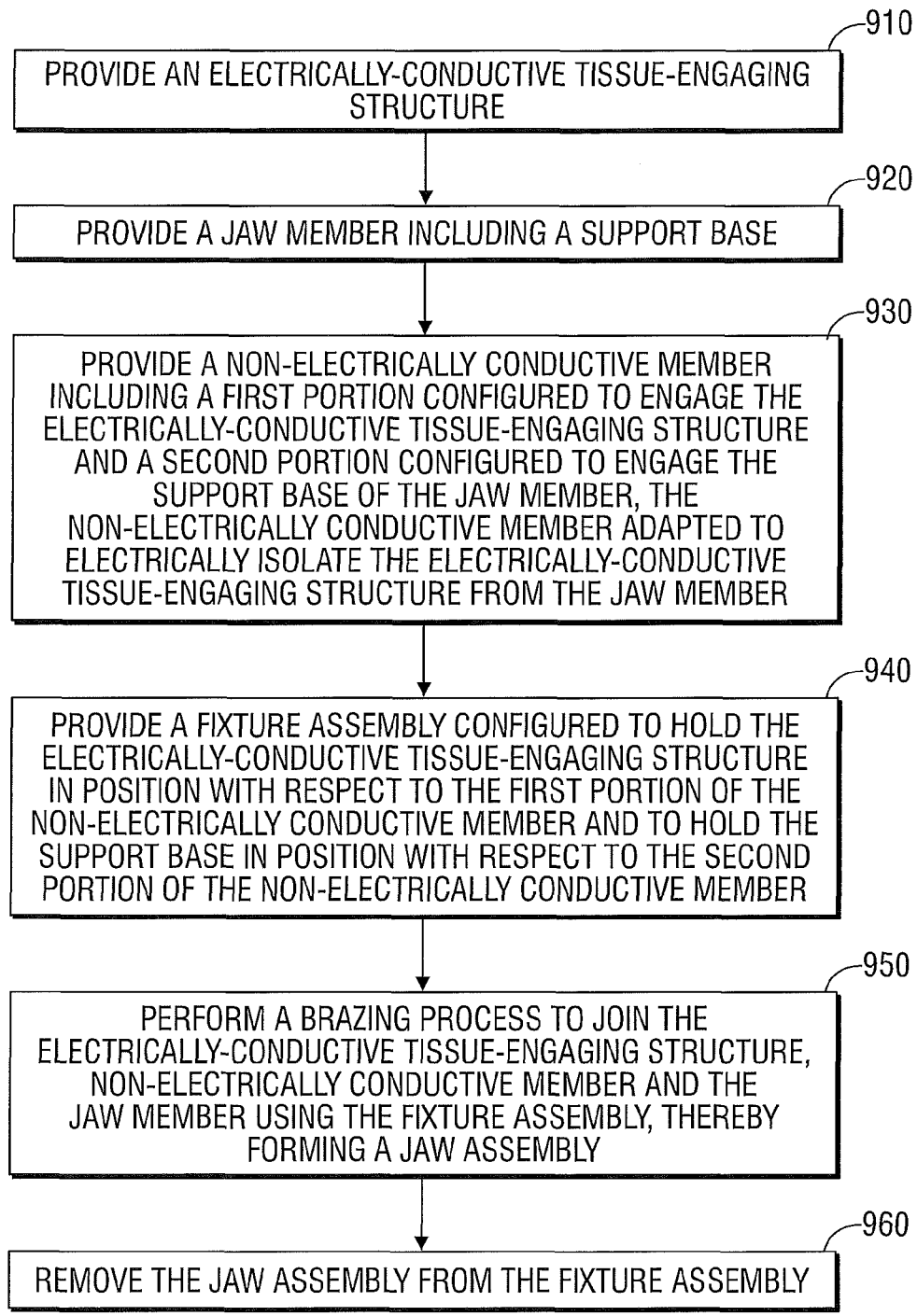
FIG. 9 is a flowchart illustrating a method of manufacturing a jaw assembly in accordance with an embodiment of the present disclosure.

FIG. 9 is a flowchart illustrating a method of manufacturing a jaw assembly 410 according to an embodiment of the present disclosure. In step 910, an electrically-conductive tissue-engaging structure 160 is provided.

In step 920, a jaw member 111 including a support base 119 is provided. In some embodiments, the jaw member 111 includes an arm member 113, wherein the support base 119 extends distally from the arm member 113. Arm member 113 may include an elongated angled slot 181a and a pivot hole 186a defined therethrough. In some embodiments, the support base 119 includes an inner-facing surface 118 configured to support at least a portion of a non-electrically conductive member 419 associated with the jaw assembly 410.

In step 930, a non-electrically conductive member 419 adapted to electrically isolate the electrically-conductive tissue-engaging structure 160 from the jaw member 111 is provided. Non-electrically conductive member 419 includes a first portion 412 configured to engage the electrically-conductive tissue-engaging structure 160 and a second portion 414 configured to engage the support base 119 of the jaw member 111.

In some embodiments, the non-electrically conductive member 419 includes a body 418 defining a first lateral side portion 446 and a second lateral side portion 447. First portion 412 of the non-electrically conductive member 419 may include a first surface 413 and a shoulder region 416 extending outwardly beyond the first surface 413 along at least a portion of the first lateral side portion 446.

In step 940, a fixture assembly 600 is provided. Fixture assembly 600 is configured to hold the electrically-conductive tissue-engaging structure 160 in position with respect to the first portion 412 of the non-electrically conductive member 419 and to hold the support base 119 in position with respect to the second portion 414 of the non-electrically conductive member 419. In some embodiments, the fixture assembly 600 includes a first fixture member 601 and a second fixture member 602.

In step 950, a brazing process (or other suitable bonding process) is performed to join the electrically-conductive tissue-engaging structure, non-electrically conductive member and the jaw member using the fixture assembly, thereby forming a jaw assembly 410. Fixture assembly 600 is adapted to releaseably and securely hold the jaw member, the electrically-conductive tissue-engaging structure, and the non-electrically conductive member in position relative to one another to facilitate the brazing process.

In step 960, the jaw assembly 410 is removed from the fixture assembly 600. It will be appreciated that additional manufacturing steps may be undertaken after the step 950, prior to the removal of the jaw assembly 410 from the fixture assembly 600 in the step 960.

The presently disclosed method of manufacturing a jaw assembly 410 may further include the step of positioning the electrically-conductive tissue-engaging structure 160 in relation to an inner wall 415 of the shoulder region 416 of the non-electrically conductive member 419.

Figure 10A:
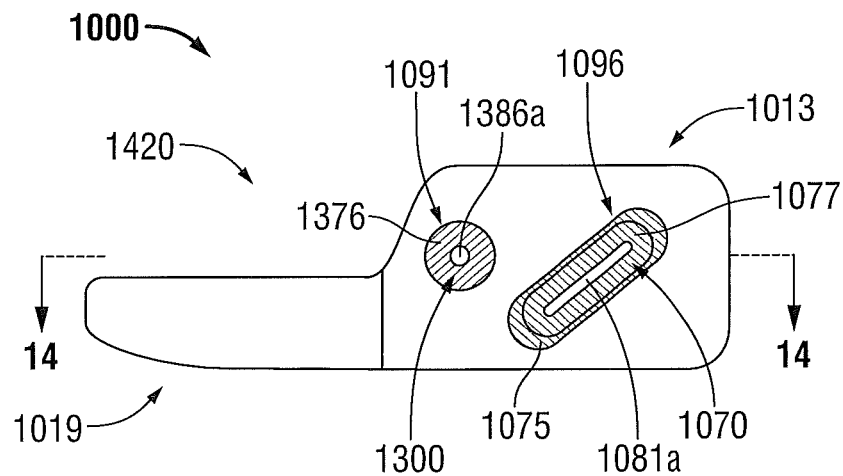
FIG. 10A is a schematic diagram of a portion of a jaw assembly including first and second electrically-insulative bushings in accordance with an embodiment of the present disclosure.

FIG. 10A shows a portion of a jaw assembly (shown generally as 1000 in FIG. 10A) in accordance with an embodiment of the present disclosure that includes a jaw member 1420 including a support base 1019 that extends distally from an arm member 1013. Arm member 1013 generally defines one or more apertures at least partially therethrough. In some embodiments, as shown in FIG. 10A, the arm member 1013 includes a first opening 1091 and a second opening or slot 1096 defined therethrough. The shape, size and location of the first opening 1091 and the second opening or slot 1096 may be varied from the configuration depicted in FIG. 10A. In alternative embodiments not shown, the jaw assembly 1000 may include additional, fewer, or different apertures than shown in FIG. 10A.

Figure 10B:
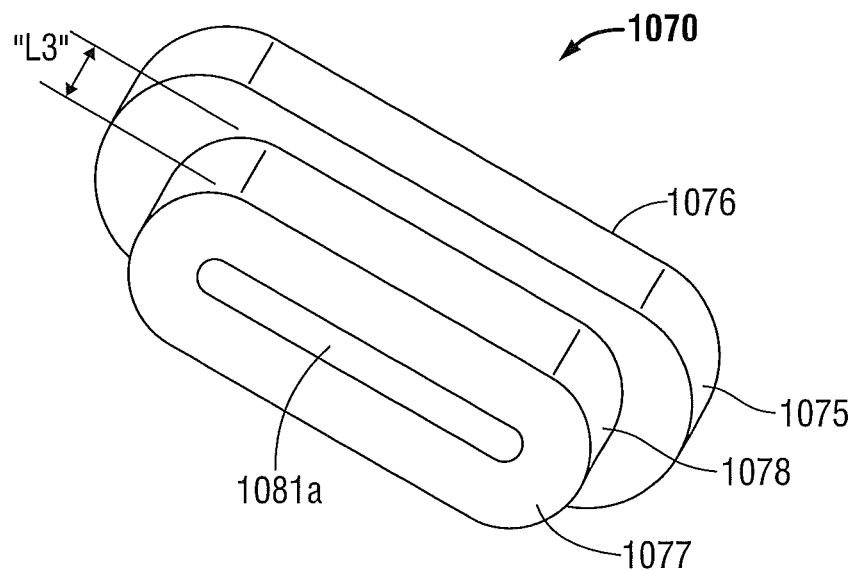
FIG. 10B is enlarged, perspective view of the second electrically-insulative bushing shown in FIG. 10A.

In some embodiments, as shown in FIG. 10A, at least a portion of a first electrically-insulative bushing 1300, which is shown in more detail in FIG. 13, is disposed within the pivot hole 1091 defining a pivot hole 1386a therethrough, and at least a portion of a second electrically-insulative bushing 1076, which is shown in more detail in FIG. 10B, is disposed within the second opening or slot 1096.

In FIG. 10B, the second electrically-insulative bushing 1070 of FIG. 10A is shown and includes a first portion 1075 including a first surface 1076, a second portion 1078 coupled to the first portion 1075, and an elongated slot 1081a defined therethrough. Second portion 1078 of the second electrically-insulative bushing 1070 has a length "L3". As shown in FIGS. 10A and 10B, the second portion 1078 of the electrically-insulative bushing 1070 includes a surface 1077. In some embodiments, the length "L3" of the second portion 1078 of the second electrically-insulative bushing 1070 is longer than the length "L6" of the arm member 1013 shown in FIG. 11C, e.g., to facilitate alignment and/or mating engagement with the electrically-insulative jaw insert 1200.

Figure 11A:
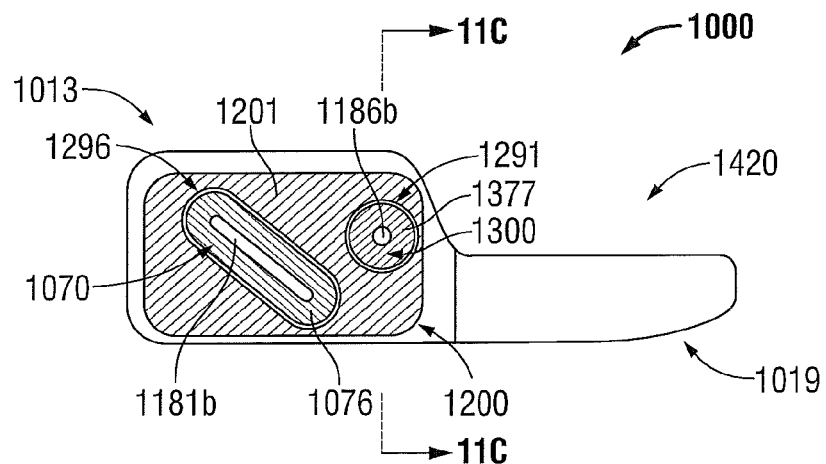
FIG. 11A is a schematic diagram of a portion of a jaw assembly including an electrically-insulative jaw insert in accordance with an embodiment of the present disclosure.

FIG. 11A shows a portion of a jaw assembly (shown generally as 1000 in FIG. 11A) that includes an electrically-insulative jaw insert 1200 in accordance with an embodiment of the present disclosure shown with the first and second electrically-insulative bushings 1300 and 1070, respectively, of FIG. 10A. The electrically-insulative jaw insert 1200 may be attached to the jaw assembly 1000 in any suitable way. In some embodiments, the electrically-insulative jaw insert 1200 may be attached to the jaw assembly 1000 using an adhesive having suitable bonding characteristics. The first electrically-insulative bushing 1300 (FIG. 13) is disposed in part within the first opening 1291 defined in the insert 1200, and the second electrically-insulative bushing 1070 is disposed in part within the second opening or slot 1296 defined in the insert 1200.

Figure 11B:
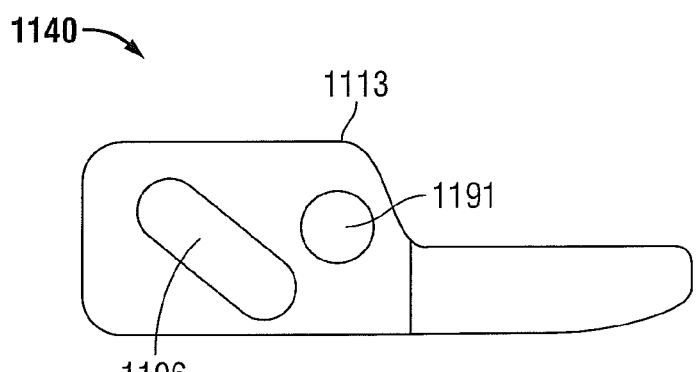
FIG. 11B is a schematic diagram of a portion of a jaw assembly in accordance with an embodiment of the present disclosure.

FIG. 11B shows a structural insert 1140 that includes a member 1113 defining a first opening 1191 and a second opening or slot 1196 therethrough. In some embodiments, the electrically-insulative bushing 1070, the electrically-insulative jaw insert 1200 and/or the electrically-insulative bushing 1300 (or other bushings) may be attached to the structural insert 1140. In some embodiments the first opening 1191 is configured to receive a portion of the electrically-insulative jaw insert 1200, and the second opening or slot 1196 may be configured to receive a portion of the electrically-insulative bushing 1070.

Figure 11C:
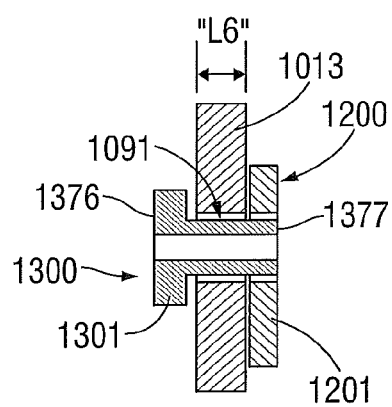
FIG. 11C is an enlarged, cross-sectional view taken along the section lines 11C-11C of FIG. 11A.

FIG. 11C shows an enlarged, cross-sectional view of a portion of the jaw assembly 1000 of FIG. 11A. In some embodiments, as shown in FIG. 11C, the first electrically-insulative bushing 1300 extends through the opening 1091 defined in the arm member 1013 of the jaw member 1420 (FIG. 11A) and the second opening or slot 1296 defined in the insert body 1201 of the insert 1200.

As best shown in FIG. 12, the electrically-insulative jaw insert 1200 includes an insert body 1201 defining a first opening 1291 and a second opening or slot 1296 therethrough. Insert 1200 may be formed from any suitable non-electrically conductive material. In some embodiments, the insert 1200 may include ceramic or any of a variety of suitable non-electrically conductive materials such as polymeric materials, e.g., plastics, and/or other insulative materials. In other embodiments, other non-electrically conductive synthetic and/or natural materials having suitable weight, strength, cost and/or other characteristics may be used for the insert 1200. In alternative embodiments not shown, the insert body 1201 may include other apertures defined at least partially therethrough.

In some embodiments, as shown in FIGS. 11A and 12, the insert body 1201 is substantially flat and planar. As shown in FIG. 11A, at least a portion of the first electrically-insulative bushing 1300 is disposed within the first opening 1291 of the insert body 1201 defining a pivot hole 1186b, and at least a portion of the second electrically-insulative bushing 1070 is disposed in the second opening or slot 1296 of the insert body 1201 defining an elongated angled slot 1181b therethrough.

FIG. 13 shows an electrically-insulative bushing 1300 in accordance with an embodiment of the present disclosure. Electrically-insulative bushing 1300 includes a first portion 1301, a second portion 1302, and an aperture or opening 1386 defined therethrough. First portion 1301 includes a first surface 1376 and an opposite second surface 1378. Second portion 1302 is coupled at one end to the second surface 1375 of the first portion 1301. Second portion 1302 includes a first surface 1377. As shown in FIG. 13, the second portion 1302 of the electrically-insulative bushing 1300 has a length "L3".

FIG. 14 shows a cross-sectional view of the jaw assembly 1000 of FIG. 10A. Jaw assembly 1000 includes the electrically-insulative jaw insert 1200 of FIG. 12, the first electrically-insulative bushing 1300 of FIG. 13, and the second electrically-insulative bushing 1070 of FIG. 10B. Insert 1200 provides electrical isolation between a first lateral face 1014 of the arm member 1013 and component(s) of a mating jaw assembly. In some embodiments, the first surface 1376 of the first portion 1301 of the first electrically-insulative bushing 1300 and the first surface 1076 of the first portion 1075 of the second electrically-insulative bushing 1070 may provide electrical isolation between a second lateral face 1015 of the arm member 1013 and component(s) of a mating jaw assembly.

In some embodiments, the jaw assembly 1000 may be provided with a non-electrically isolated insert (e.g., 1113 shown in FIG. 15). This configuration provides an alternative way to electrically isolate the upper and lower jaw assemblies, e.g., as opposed to the embodiment shown in FIGS. 4-8, which utilizes an isolated sealing plate 160. With the use of a non-electrically isolated insert 1113, an isolated sealing plate 160 is not required, and the distal end of the jaw member 1420 may be entirely or selectively (e.g., by coating) electrically active.

FIG. 15 shows a cross-sectional view of an end-effector assembly (shown generally as 1500 in FIG. 15) including the jaw member 1420 in accordance with an embodiment of the present disclosure. Arm member 1013 and the support base 1019 of the jaw member 1420 of the lower jaw assembly are electrically-isolated from the opposing arm member 2113 of the upper jaw assembly (partially shown in FIG. 15) by the first electrically-insulative bushing 1300 and the second electrically-insulative bushing 1070. Arm member 1013 and the support base 1019 of the jaw member 1420 of the lower jaw assembly are electrically-isolated from shafts 1505 and 1508 by the insert 1200, and electrically-isolated from pins 1503 and 1504 by the first electrically-insulative bushing 1300 and the second electrically-insulative bushing 1070.

FIG. 16A shows an electrically-insulative bushing 1600 in accordance with an embodiment of the present disclosure. Electrically-insulative bushing 1600 includes a first portion 1601, a second portion 1602 coupled to the first portion 1601, and an aperture or opening 1686 defined therethrough. Second portion 1602 of the electrically-insulative bushing 1600 has a length "L4". In some embodiments, the length "L4" of the second portion 1602 of the electrically-insulative bushing 1600 shown in FIG. 16A is approximately one-half or less than the length "L3" of the second portion 1302 of the electrically-insulative bushing 1300 of FIG. 13.

FIG. 16B shows an electrically-insulative bushing 1610 in accordance with an embodiment of the present disclosure. Electrically-insulative bushing 1610 includes a first portion 1611, a second portion 1612 coupled to the first portion 1611, and an elongated slot 1696 defined therethrough. In some embodiments, as shown in FIG. 16B, the second portion 1602 of the electrically-insulative bushing 1600 has a length "L4".

FIG. 17A is a perspective view of electrically-insulative tubular bushing 1700 in accordance with an embodiment of the present disclosure. Electrically-insulative tubular bushing 1700 has a substantially cylindrical shape and defines an aperture or opening 1786 therethrough. As shown in FIG. 17A, the electrically-insulative tubular bushing 1700 has a length "L5". In some embodiments, the length "L5" of the electrically-insulative tubular bushing 1700 shown in FIG. 17A is substantially equal to or greater than the length "L3" of the second portion 1302 of the first electrically-insulative bushing 1300 of FIG. 13. Although the electrically-insulative tubular bushing 1700 shown in FIG. 17A has a substantially cylindrical shape, other suitable shapes may be utilized.

FIG. 17B shows an oblong electrically-insulative bushing 1710 in accordance with an embodiment of the present disclosure. Electrically-insulative bushing 1710 includes a body 1712 and an elongated slot 1796 defined therethrough. Body 1712 of the electrically-insulative bushing 1710 has a length "L5".

Figure 18:
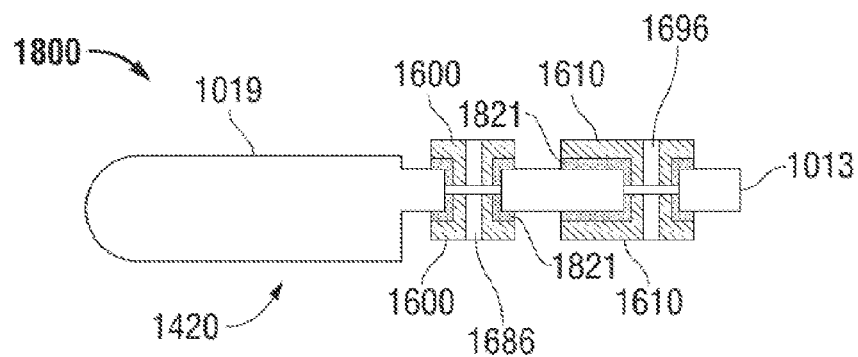
FIG. 18 is an enlarged, cross-sectional view of a jaw assembly including two of the electrically-insulative bushings shown in FIG. 16A and two of the electrically-insulative bushings shown in FIG. 16B in accordance with an embodiment of the present disclosure.

FIG. 18 shows a portion of a jaw assembly (shown generally as 1800 in FIG. 18) in accordance with an embodiment of the present disclosure that includes the jaw member 1420 including a support base 1019 that extends distally from an arm member 1013. Jaw assembly 1800 includes two of the bushings 1600 and two of the bushings 1610, shown in FIGS. 16A and 16B, respectively, disposed in axial alignment with one another on opposite lateral sides of the arm member 1013. The bushings 1600 and 1610 may be attached to the arm member 1013 in any suitable way. In some embodiments, the bushings 1600 and 1610 may be attached to the arm member 1013 using an adhesive 1821 having suitable bonding characteristics. In alternative embodiments not shown, the jaw assembly 1800 may be used in the end effector assembly 1500 of FIG. 15, i.e., in lieu of the jaw assembly 1000.

Figure 19:
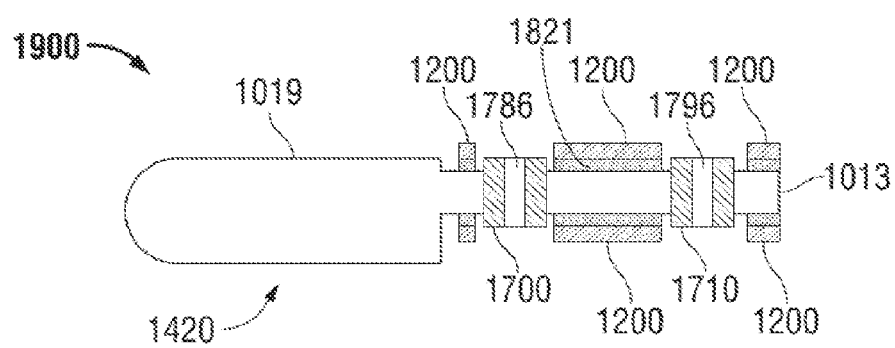
FIG. 19 is an enlarged, cross-sectional view of a jaw assembly including the electrically-insulative tubular bushing shown in FIG. 17A and the oblong electrically-insulative bushing shown in FIG. 17B in accordance with an embodiment of the present disclosure.

FIG. 19 shows a portion of a jaw assembly (shown generally as 1900 in FIG. 19) including the jaw member 1420 in accordance with an embodiment of the present disclosure. Jaw assembly 1900 includes two of the electrically-insulative jaw insert 1200. Jaw assembly 1900 includes the tubular bushing 1700 of FIG. 17A disposed in the first opening 1291 defined in the arm member 1013 of the jaw member 1420, and the oblong bushing 1710 of FIG. 17B disposed in second opening or slot 1296 defined in the arm member 1013. In alternative embodiments not shown, the jaw assembly 1900 may be used in the end effector assembly 1500 of FIG. 15, i.e., in lieu of the jaw assembly 1000.

Figure 20:
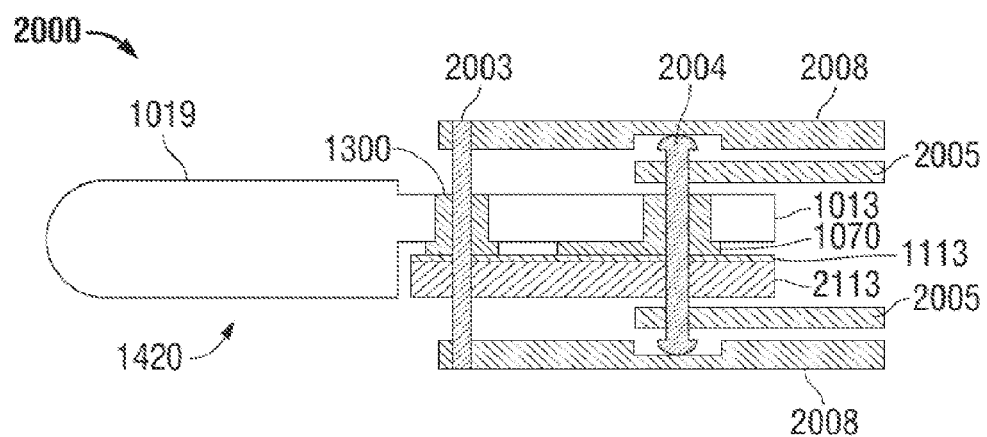
FIG. 20 an enlarged, cross-sectional view of an end-effector assembly including the jaw assembly of FIG. 19 in accordance with an embodiment of the present disclosure.

FIG. 20 shows a cross-sectional view of an end-effector assembly (shown generally as 2000 in FIG. 20) in accordance with an embodiment of the present disclosure that includes the jaw member 1420 including a support base 1019 that extends distally from an arm member 1013. Arm member 1013 is electrically-isolated from the pins 2003 and 2004 and from the opposing arm member 2113 by the first electrically-insulative bushing 1300 and the second electrically-insulative bushing 1070. Arm member 1013 is electrically-isolated from tubes 2005 and 2008 by forming tube 2005 from a suitable non-electrically conductive material.

In any of the above-described embodiments, e.g., as shown in FIGS. 10A through 20, brazing or other suitable bonding methods may used. Any suitable fixture may be used, e.g., fixture assembly 600 shown in FIG. 6, in connection with brazing and/or adhesive bonding, or other suitable bonding process.

The above-described bipolar forceps is capable of directing energy into tissue, and may be suitable for use in a variety of procedures and operations. The above-described end-effector embodiments may utilize both mechanical clamping action and electrical energy to effect hemostasis by heating tissue and blood vessels to coagulate, cauterize, cut and/or seal tissue. The jaw assemblies may be either unilateral or bilateral. The above-described bipolar forceps embodiments may be suitable for utilization with endoscopic surgical procedures and/or hand-assisted, endoscopic and laparoscopic surgical procedures. The above-described bipolar forceps embodiments may be suitable for utilization in open surgical applications.

The above-described method of manufacturing a jaw assembly may result in the formation of jaw assemblies that meet specific tolerance requirements for proper jaw alignment and other tightly-toleranced jaw assembly features. The above-described method of manufacturing a jaw assembly may provide improved thermal resistance, strength and rigidity of jaw assemblies using lower cost technologies.

The above-described non-electrically conductive members may be used for joining together sealing plates and support bases of jaw members of varied geometries, e.g., lengths and curvatures, such that variously-configured jaw assemblies may be fabricated and assembled into various end-effector configurations, e.g., depending upon design of specialized electrosurgical instruments.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A jaw assembly comprising:
   first and second jaw members, each of the first and second jaw members including:
      an electrically-conductive tissue-engaging structure;
      an arm member;
      a support base extending from the arm member; and
      a non-electrically conductive member including a first portion configured to engage the electrically-conductive tissue-engaging structure and a second portion configured to engage the support base, the non-electrically conductive member adapted to electrically isolate the electrically-conductive tissue-engaging structure from the support base,
      wherein the electrically-conductive tissue-engaging structure and the non-electrically conductive member cooperatively define a longitudinally-oriented knife channel therethrough;
   an electrically insulative jaw insert attached to one of the arm members; and
   an electrically insulative bushing having a first part and a second part, the first part larger than the second part and positioned between the jaw members and configured to electrically isolate the first jaw member from the second jaw member, the second part disposed in the electrically insulative jaw insert.

2. The jaw assembly of claim 1, wherein the electrically-conductive tissue-engaging structure includes a first portion and a second portion, the first and second portions at least partially separated by the longitudinally-oriented knife channel.

3. The jaw assembly of claim 1, wherein the non-electrically conductive member includes a body defining a first lateral side portion having a first length and a second lateral side portion having a second length.

4. The jaw assembly of claim 3, wherein the first and second lateral side portions are joined at one end by an apex disposed at a distal end of the body and spaced apart at opposing ends to define an opening therebetween.

5. The jaw assembly of claim 4, wherein the opening is configured to receive at least a portion of the support base of the corresponding jaw member therein.

6. The jaw assembly of claim 3, wherein the non-electrically conductive member further includes an upper portion disposed between the first and second lateral side portions.

7. The jaw assembly of claim 6, wherein the upper portion includes a U-shaped wall portion that defines the longitudinally-oriented knife channel.

8. An end-effector assembly, comprising:
   opposing first and second jaw assemblies pivotably mounted with respect to one another, wherein the first jaw assembly includes a first jaw member and the second jaw assembly includes a second jaw member;
   the first jaw member including:
      a first arm member defining at least one aperture at least partially therethrough; and
      a first support base extending distally from the first arm member;
   the second jaw member including:
      a second arm member defining at least one aperture at least partially therethrough; and
      a second support base extending distally from the second arm member;
   the first jaw assembly further including:
      a first electrically-conductive tissue-engaging structure; and
      a first non-electrically conductive member including a first portion configured to engage the first electrically-conductive tissue-engaging structure and a second portion configured to engage the first support base of the first jaw member;
   the second jaw assembly further including:
      a second electrically-conductive tissue-engaging structure; and
      a second non-electrically conductive member including a first portion configured to engage the second electrically-conductive tissue-engaging structure and a second portion configured to engage the second support base of the second jaw member;
   at least one pivot pin engaged with the apertures of the first and second jaw members such that the first and second jaw assemblies are pivotably mounted with respect to one another;
   an electrically insulative jaw insert attached to the first arm member; and
   an electrically insulative bushing having a first part and a second part, the first part larger than the second part and positioned between the first and second arm members and configured to electrically isolate the first jaw member from the second jaw member, the second part disposed in the electrically insulative jaw insert.

9. The end-effector assembly of claim 8, wherein the first electrically-conductive tissue-engaging structure and the first non-electrically conductive member cooperatively define a longitudinally-oriented knife channel therethrough.

10. The end-effector assembly of claim 8, wherein the first non-electrically conductive member includes a body defining a first lateral side portion and a second lateral side portion, the first and second lateral side portions joined at one end by an apex disposed at a distal end of the body and spaced apart at opposing ends to define an opening therebetween.

11. The end-effector assembly of claim 10, wherein the opening is configured to receive at least a portion of the first support base of the first jaw member therein.

12. The end-effector assembly of claim 8, wherein the second jaw assembly is adapted to connect the second electrically-conductive tissue-engaging structure associated therewith to an electrosurgical generator.

13. An end-effector assembly, comprising:
   a first jaw assembly having a first jaw member including:
      a first arm member defining a first aperture at least partially therethrough; and
      a first support base extending distally from the first arm member;
   a second jaw assembly having a second jaw member including:
      a second arm member defining a second aperture at least partially therethrough; and
      a second support base extending distally from the second arm member;
   a pivot pin engaged with the first and second apertures such that the first and second jaw assemblies are pivotably mounted with respect to one another;
   an electrically insulative jaw insert attached to the first arm member; and
   an electrically insulative bushing having a first part and a second part, the first part larger than the second part and positioned between the first and second arm members and configured to electrically isolate the first jaw member from the second jaw member, the second part disposed in the electrically insulative jaw insert.

14. The end-effector assembly of claim 13, wherein the first jaw assembly further includes a first electrically-conductive tissue-engaging structure and the second jaw assembly further includes a second electrically-conductive tissue-engaging structure in opposition to the first electrically-conductive tissue-engaging structure.

15. The end-effector assembly of claim 14, wherein the first electrically-conductive tissue-engaging structure is supported on the first support base and the second electrically-conductive tissue-engaging structure is supported on the second support base.

* * * * *